US009510872B2

(12) United States Patent
Donner et al.

(10) Patent No.: US 9,510,872 B2
(45) Date of Patent: Dec. 6, 2016

(54) SPINAL STABILIZATION SYSTEM

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 14/209,138

(22) Filed: Mar. 13, 2014

(65) Prior Publication Data

US 2014/0296917 A1    Oct. 2, 2014

Related U.S. Application Data

(60) Provisional application No. 61/794,543, filed on Mar. 15, 2013.

(51) Int. Cl.
*A61B 17/70* (2006.01)

(52) U.S. Cl.
CPC ....... *A61B 17/7071* (2013.01); *A61B 17/7043* (2013.01); *A61B 17/7026* (2013.01); *A61B 17/7067* (2013.01)

(58) Field of Classification Search
CPC .......... A61B 17/7062; A61B 17/7071
USPC .................. 606/246–253
See application file for complete search history.

(56) References Cited

U.S. PATENT DOCUMENTS

| 4,488,542 A | 12/1984 | Helland |
| 4,569,338 A | 2/1986 | Edwards |
| 4,590,928 A | 5/1986 | Hunt et al. |
| 4,714,469 A | 12/1987 | Kenna et al. |
| 4,773,402 A | 9/1988 | Asher et al. |
| 4,794,918 A | 1/1989 | Wolter |
| 4,920,958 A | 5/1990 | Walt et al. |
| 4,950,270 A | 8/1990 | Bowman et al. |
| 5,026,373 A | 6/1991 | Ray et al. |
| 5,192,327 A | 3/1993 | Brantigan |
| 5,242,444 A | 9/1993 | MacMillan |
| 5,282,861 A | 2/1994 | Kaplan et al. |

(Continued)

FOREIGN PATENT DOCUMENTS

| AU | 1753200 A | 8/2000 |
| CN | 2265765 Y | 10/1997 |

(Continued)

OTHER PUBLICATIONS

International Search Report and Written Opinion dated Aug. 19, 2014 from corresponding International patent application.

*Primary Examiner* — Ellen C Hammond
*Assistant Examiner* — Stuart S Bray
(74) *Attorney, Agent, or Firm* — Glenn H. Lenzen; Dietze and Davis, P.C.

(57) ABSTRACT

A spinal stabilization system is provided for maintaining preselected spacing and movement between adjacent vertebrae in a spinal column and for providing overall stability thereto. The system includes interlaminar members positioned in the spaces intermediate a first vertebra and the vertebrae positioned immediately above and immediately below and adjacent to the first vertebra. The interlaminar members are operatively connected to one another by an adjustable support structure and cooperate therewith to maintain the preselected spacing between adjacent vertebrae and to provide overall stability to the spinal column.

24 Claims, 13 Drawing Sheets

(56) References Cited

U.S. PATENT DOCUMENTS

| | | | |
|---|---|---|---|
| 5,334,205 A | 8/1994 | Cain | |
| 5,336,225 A | 8/1994 | Zang | |
| 5,415,661 A * | 5/1995 | Holmes | 606/255 |
| 5,437,674 A | 8/1995 | Worcel et al. | |
| 5,443,509 A | 8/1995 | Boucher et al. | |
| 5,456,267 A | 10/1995 | Stark | |
| 5,593,407 A | 1/1997 | Reis | |
| 5,607,424 A | 3/1997 | Tropiano et al. | |
| 5,609,635 A | 3/1997 | Michelson | |
| 5,609,636 A | 3/1997 | Kohrs et al. | |
| 5,626,434 A | 5/1997 | Cook | |
| 5,645,599 A * | 7/1997 | Samani | 623/17.16 |
| 5,658,337 A | 8/1997 | Kohrs et al. | |
| 5,669,909 A | 9/1997 | Zdeblick et al. | |
| 5,688,284 A | 11/1997 | Chervitz et al. | |
| 5,702,452 A | 12/1997 | Argenson | |
| 5,743,914 A | 4/1998 | Skiba | |
| 5,772,594 A | 6/1998 | Barrick et al. | |
| 5,919,193 A | 7/1999 | Slavitt | |
| 5,928,239 A | 7/1999 | Mirza et al. | |
| 5,993,463 A | 11/1999 | Truwit et al. | |
| 6,053,916 A | 4/2000 | Moore et al. | |
| 6,063,442 A | 5/2000 | Cohen et al. | |
| 6,175,758 B1 | 1/2001 | Kambin | |
| 6,236,891 B1 | 5/2001 | Ingle et al. | |
| 6,302,885 B1 | 10/2001 | Essiger | |
| 6,322,562 B1 | 11/2001 | Wolter | |
| 6,413,278 B1 | 7/2002 | Marchosky | |
| 6,432,107 B1 | 8/2002 | Ferree | |
| 6,547,795 B2 | 4/2003 | Schneiderman | |
| 6,547,823 B2 | 4/2003 | Scarborough et al. | |
| 6,565,605 B2 * | 5/2003 | Goble et al. | 623/17.11 |
| 6,579,318 B2 | 6/2003 | Varga et al. | |
| 6,607,487 B2 | 8/2003 | Chang et al. | |
| 6,635,059 B2 | 10/2003 | Randall et al. | |
| 6,660,224 B2 | 12/2003 | Lefebvre et al. | |
| 6,669,698 B1 | 12/2003 | Tromanhauser et al. | |
| 6,682,563 B2 | 1/2004 | Scharf | |
| 6,682,567 B1 | 1/2004 | Schroeder | |
| 6,716,245 B2 | 4/2004 | Pasquet et al. | |
| 6,723,099 B1 | 4/2004 | Goshert | |
| 6,743,256 B2 | 6/2004 | Mason | |
| 6,746,451 B2 | 6/2004 | Middleton et al. | |
| 6,824,564 B2 | 11/2004 | Crozet | |
| 6,835,208 B2 | 12/2004 | Marchosky | |
| 6,855,167 B2 | 2/2005 | Shimp et al. | |
| 6,902,567 B2 | 6/2005 | Del Medico | |
| 6,908,465 B2 | 6/2005 | von Hoffmann et al. | |
| 6,945,488 B2 | 9/2005 | Shimanuki et al. | |
| 6,974,461 B1 | 12/2005 | Wolter | |
| 7,011,660 B2 | 3/2006 | Sherman et al. | |
| 7,087,058 B2 | 8/2006 | Cragg | |
| 7,108,828 B2 | 9/2006 | Lefebvre et al. | |
| 7,201,775 B2 | 4/2007 | Gorensek et al. | |
| 7,208,222 B2 | 4/2007 | Rolfe et al. | |
| 7,217,291 B2 | 5/2007 | Zucherman et al. | |
| 7,235,101 B2 | 6/2007 | Berry et al. | |
| 7,255,712 B1 | 8/2007 | Steinberg | |
| 7,331,995 B2 | 2/2008 | Eisermann et al. | |
| 7,396,360 B2 | 7/2008 | Lieberman | |
| 7,410,501 B2 | 8/2008 | Michelson | |
| 7,458,991 B2 | 12/2008 | Wang et al. | |
| 7,465,317 B2 | 12/2008 | Malberg et al. | |
| 7,575,600 B2 | 8/2009 | Zucherman et al. | |
| 7,621,939 B2 | 11/2009 | Zucherman et al. | |
| 7,635,447 B2 | 12/2009 | Hamman et al. | |
| 7,637,954 B2 | 12/2009 | Michelson | |
| 7,648,509 B2 | 1/2010 | Stark | |
| 7,666,209 B2 | 2/2010 | Zucherman et al. | |
| 7,699,873 B2 * | 4/2010 | Stevenson et al. | 606/250 |
| 7,704,279 B2 | 4/2010 | Moskowitz et al. | |
| 7,740,795 B2 | 6/2010 | Wang et al. | |
| 7,789,895 B2 | 9/2010 | Heinz | |
| 7,794,465 B2 | 9/2010 | Marik et al. | |
| 7,799,081 B2 | 9/2010 | McKinley | |
| 7,819,869 B2 | 10/2010 | Godara et al. | |
| 7,824,404 B2 | 11/2010 | Godara et al. | |
| 7,837,732 B2 | 11/2010 | Zucherman et al. | |
| 7,837,734 B2 | 11/2010 | Zucherman et al. | |
| 7,846,162 B2 | 12/2010 | Nelson et al. | |
| 7,850,719 B2 | 12/2010 | Gournay et al. | |
| 7,850,732 B2 | 12/2010 | Heinz | |
| 7,909,871 B2 | 3/2011 | Abdou | |
| 7,922,765 B2 | 4/2011 | Reiley | |
| 7,972,382 B2 | 7/2011 | Foley et al. | |
| 8,075,561 B2 | 12/2011 | Wolter | |
| 8,162,981 B2 | 4/2012 | Vestgaarden | |
| 8,221,428 B2 | 7/2012 | Trieu | |
| 8,262,697 B2 * | 9/2012 | Kirschman | 606/248 |
| 8,568,453 B2 * | 10/2013 | Abdou | 606/248 |
| 8,801,757 B2 * | 8/2014 | Abdou | 606/248 |
| 2001/0005796 A1 | 6/2001 | Zdeblick et al. | |
| 2002/0032484 A1 | 3/2002 | Hyde, Jr. | |
| 2002/0087161 A1 | 7/2002 | Randall et al. | |
| 2002/0116000 A1 * | 8/2002 | Zucherman et al. | 606/61 |
| 2002/0147449 A1 * | 10/2002 | Yun | 606/61 |
| 2002/0183846 A1 | 12/2002 | Kuslich et al. | |
| 2003/0109928 A1 | 6/2003 | Pasquet et al. | |
| 2003/0114931 A1 | 6/2003 | Lee et al. | |
| 2003/0171750 A1 * | 9/2003 | Chin | 606/61 |
| 2004/0073216 A1 | 4/2004 | Lieberman | |
| 2004/0117017 A1 * | 6/2004 | Pasquet et al. | 623/17.11 |
| 2004/0220668 A1 | 11/2004 | Eisermann et al. | |
| 2004/0228901 A1 | 11/2004 | Trieu et al. | |
| 2005/0033434 A1 * | 2/2005 | Berry | 623/17.14 |
| 2005/0131409 A1 * | 6/2005 | Chervitz et al. | 606/61 |
| 2005/0149192 A1 | 7/2005 | Zucherman et al. | |
| 2005/0154391 A1 | 7/2005 | Doherty et al. | |
| 2005/0203515 A1 | 9/2005 | Doherty et al. | |
| 2005/0240264 A1 | 10/2005 | Tokish et al. | |
| 2005/0245925 A1 | 11/2005 | Iki et al. | |
| 2005/0267482 A1 | 12/2005 | Hyde | |
| 2005/0273099 A1 | 12/2005 | Baccelli et al. | |
| 2006/0015181 A1 | 1/2006 | Elberg | |
| 2006/0054171 A1 | 3/2006 | Dall | |
| 2006/0069438 A1 | 3/2006 | Zucherman et al. | |
| 2006/0069439 A1 | 3/2006 | Zucherman et al. | |
| 2006/0095134 A1 | 5/2006 | Trieu et al. | |
| 2006/0142759 A1 * | 6/2006 | Arnin et al. | 606/61 |
| 2006/0147332 A1 | 7/2006 | Jones et al. | |
| 2006/0161154 A1 | 7/2006 | McAfee | |
| 2006/0217718 A1 * | 9/2006 | Chervitz et al. | 606/61 |
| 2006/0224159 A1 * | 10/2006 | Anderson | 606/61 |
| 2006/0241601 A1 * | 10/2006 | Trautwein et al. | 606/61 |
| 2006/0241642 A1 * | 10/2006 | Arnin et al. | 606/90 |
| 2006/0241757 A1 * | 10/2006 | Anderson | 623/17.11 |
| 2007/0027543 A1 | 2/2007 | Gimble et al. | |
| 2007/0055374 A1 | 3/2007 | Copf et al. | |
| 2007/0123861 A1 | 5/2007 | Dewey | |
| 2007/0156241 A1 | 7/2007 | Reiley et al. | |
| 2007/0162000 A1 * | 7/2007 | Perkins | 606/61 |
| 2007/0162134 A1 | 7/2007 | Marnay et al. | |
| 2007/0179621 A1 | 8/2007 | McClellan et al. | |
| 2007/0198093 A1 | 8/2007 | Brodke et al. | |
| 2007/0233068 A1 | 10/2007 | Bruneau | |
| 2007/0233129 A1 | 10/2007 | Bertagnoli | |
| 2007/0265621 A1 | 11/2007 | Matthis et al. | |
| 2007/0270879 A1 | 11/2007 | Isaza et al. | |
| 2008/0009861 A1 | 1/2008 | Stark | |
| 2008/0015609 A1 | 1/2008 | Trautwein | |
| 2008/0021454 A1 | 1/2008 | Chao et al. | |
| 2008/0021455 A1 | 1/2008 | Chao et al. | |
| 2008/0021456 A1 | 1/2008 | Gupta et al. | |
| 2008/0039843 A1 | 2/2008 | Abdou | |
| 2008/0065215 A1 | 3/2008 | Reiley | |
| 2008/0140082 A1 | 6/2008 | Erdem et al. | |
| 2008/0177264 A1 * | 7/2008 | Alamin et al. | 606/74 |
| 2008/0177326 A1 * | 7/2008 | Thompson | 606/277 |
| 2008/0228225 A1 * | 9/2008 | Trautwein et al. | 606/246 |
| 2008/0228276 A1 | 9/2008 | Mathews et al. | |
| 2008/0234733 A1 * | 9/2008 | Scrantz et al. | 606/246 |
| 2008/0269904 A1 * | 10/2008 | Voorhies | 623/17.16 |
| 2008/0281361 A1 | 11/2008 | Vittur | |
| 2008/0288081 A1 | 11/2008 | Scrafton et al. | |

(56) References Cited

U.S. PATENT DOCUMENTS

| | | |
|---|---|---|
| 2008/0300685 A1 | 12/2008 | Carls et al. |
| 2008/0306525 A1* | 12/2008 | Mitchell et al. ............... 606/246 |
| 2009/0018660 A1 | 1/2009 | Roush |
| 2009/0018662 A1* | 1/2009 | Pasquet et al. ............. 623/17.16 |
| 2009/0024169 A1* | 1/2009 | Triplett et al. ................ 606/248 |
| 2009/0024174 A1 | 1/2009 | Stark |
| 2009/0076553 A1 | 3/2009 | Wolter |
| 2009/0088849 A1 | 4/2009 | Armstrong et al. |
| 2009/0099610 A1 | 4/2009 | Johnson et al. |
| 2009/0131986 A1 | 5/2009 | Lee et al. |
| 2009/0138048 A1* | 5/2009 | Baccelli et al. ............... 606/263 |
| 2009/0138053 A1 | 5/2009 | Assell et al. |
| 2009/0149885 A1* | 6/2009 | Durward et al. .............. 606/246 |
| 2009/0187217 A1 | 7/2009 | Weiman |
| 2009/0202150 A1 | 8/2009 | Fradkin et al. |
| 2009/0204151 A1 | 8/2009 | Bracken |
| 2009/0216238 A1 | 8/2009 | Stark |
| 2009/0216276 A1* | 8/2009 | Pasquet ........................ 606/249 |
| 2009/0259261 A1* | 10/2009 | Reiley ........................... 606/329 |
| 2009/0264929 A1* | 10/2009 | Alamin et al. ................ 606/248 |
| 2009/0270920 A1* | 10/2009 | Douget et al. ................ 606/254 |
| 2009/0287254 A1 | 11/2009 | Nayet et al. |
| 2009/0292314 A1* | 11/2009 | Mangione et al. ............ 606/249 |
| 2009/0306671 A1 | 12/2009 | McCormack et al. |
| 2010/0010496 A1* | 1/2010 | Isaza et al. ..................... 606/96 |
| 2010/0049252 A1 | 2/2010 | Smisson |
| 2010/0069965 A1* | 3/2010 | Abdou .......................... 606/279 |
| 2010/0094290 A1 | 4/2010 | Vaidya |
| 2010/0100135 A1 | 4/2010 | Phan |
| 2010/0106200 A1 | 4/2010 | Stark |
| 2010/0131011 A1 | 5/2010 | Stark |
| 2010/0137919 A1 | 6/2010 | Wolter |
| 2010/0152785 A1 | 6/2010 | Forton et al. |
| 2010/0179552 A1 | 7/2010 | Wolter |
| 2010/0268228 A1 | 10/2010 | Petersen |
| 2010/0292738 A1 | 11/2010 | Reiley |
| 2010/0292800 A1 | 11/2010 | Zubok |
| 2010/0305702 A1 | 12/2010 | Michelson |
| 2010/0331981 A1 | 12/2010 | Mohammed |
| 2011/0009869 A1 | 1/2011 | Marino et al. |
| 2011/0034957 A1* | 2/2011 | Biedermann .................. 606/305 |
| 2011/0071568 A1* | 3/2011 | Ginn et al. .................... 606/249 |
| 2011/0071635 A1 | 3/2011 | Zhang et al. |
| 2011/0087294 A1 | 4/2011 | Reiley |
| 2011/0087296 A1 | 4/2011 | Reiley et al. |
| 2011/0098816 A1 | 4/2011 | Jacob et al. |
| 2011/0098817 A1 | 4/2011 | Eckhardt et al. |
| 2011/0106163 A1* | 5/2011 | Hochschuler et al. ........ 606/264 |
| 2011/0106257 A1 | 5/2011 | Matge |
| 2011/0118785 A1 | 5/2011 | Reiley |
| 2011/0118790 A1 | 5/2011 | Reiley |
| 2011/0118796 A1 | 5/2011 | Reiley et al. |
| 2011/0118841 A1 | 5/2011 | Reiley |
| 2011/0125268 A1 | 5/2011 | Reiley |
| 2011/0137345 A1 | 6/2011 | Stoll |
| 2011/0160772 A1* | 6/2011 | Arcenio et al. ............... 606/248 |
| 2011/0166575 A1 | 7/2011 | Assell et al. |
| 2011/0184518 A1 | 7/2011 | Trieu |
| 2011/0184520 A1 | 7/2011 | Trieu |
| 2011/0185306 A1 | 7/2011 | Aravamudan |
| 2011/0190819 A1 | 8/2011 | Trautwein |
| 2011/0196427 A1 | 8/2011 | Trautwein |
| 2011/0218571 A1* | 9/2011 | Attia ............................. 606/248 |
| 2011/0230966 A1 | 9/2011 | Trieu |
| 2011/0264229 A1 | 10/2011 | Donner |
| 2012/0022535 A1 | 1/2012 | Mayer et al. |
| 2012/0022595 A1 | 1/2012 | Pham et al. |
| 2012/0065683 A1* | 3/2012 | Kuo et al. ..................... 606/248 |
| 2012/0078303 A1 | 3/2012 | Malek |
| 2012/0095560 A1 | 4/2012 | Donner |
| 2012/0109198 A1* | 5/2012 | Dryer et al. .................. 606/248 |
| 2012/0109202 A1* | 5/2012 | Kretzer et al. ................ 606/248 |
| 2012/0130427 A1* | 5/2012 | Hoffman et al. ............. 606/248 |
| 2012/0136390 A1* | 5/2012 | Butler et al. .................. 606/248 |
| 2012/0150228 A1* | 6/2012 | Zappacosta et al. .......... 606/248 |
| 2012/0158060 A1* | 6/2012 | Abrahams et al. ........... 606/248 |
| 2012/0184997 A1* | 7/2012 | Simonson ..................... 606/265 |
| 2012/0215262 A1* | 8/2012 | Culbert et al. ................ 606/279 |
| 2012/0226312 A1* | 9/2012 | Thalgott et al. .............. 606/246 |
| 2012/0226314 A1* | 9/2012 | Chin et al. .................... 606/249 |
| 2012/0253398 A1 | 10/2012 | Metcalf et al. |
| 2012/0259370 A1* | 10/2012 | Vaidya .......................... 606/281 |
| 2012/0296428 A1* | 11/2012 | Donner ...................... 623/17.11 |
| 2013/0018427 A1 | 1/2013 | Pham et al. |
| 2013/0023933 A1* | 1/2013 | Haas .............................. 606/248 |
| 2013/0030467 A1* | 1/2013 | Karas et al. ................... 606/248 |
| 2013/0035727 A1* | 2/2013 | Datta ............................ 606/279 |
| 2013/0053854 A1* | 2/2013 | Schoenefeld et al. ........... 606/87 |
| 2013/0053902 A1 | 2/2013 | Trudeau |
| 2013/0072979 A1* | 3/2013 | Butler et al. .................. 606/248 |
| 2013/0296939 A1* | 11/2013 | Perkins ......................... 606/249 |
| 2013/0345753 A1 | 12/2013 | Kretzer |
| 2014/0052183 A1* | 2/2014 | Freese ........................... 606/248 |
| 2014/0074166 A1 | 3/2014 | Scarrow |
| 2014/0316467 A1* | 10/2014 | Siegal et al. .................. 606/249 |
| 2015/0012040 A1* | 1/2015 | Agarwal et al. .............. 606/248 |
| 2015/0182263 A1* | 7/2015 | Donner et al. ................ 606/248 |

FOREIGN PATENT DOCUMENTS

| | | |
|---|---|---|
| CN | 201139628 Y | 10/2008 |
| CN | 201275132 Y | 7/2009 |
| CN | 201275133 Y | 7/2009 |
| CN | 201275134 Y | 7/2009 |
| DE | D606195 | 12/2009 |
| KR | 101037206 B1 | 5/2011 |
| RU | 2364359 C1 | 8/2009 |
| WO | 93/08745 A1 | 5/1993 |
| WO | 95/23559 | 9/1995 |
| WO | 01/95823 A1 | 12/2001 |
| WO | 02/03895 A1 | 1/2002 |
| WO | 02/067759 A2 | 9/2002 |
| WO | 2006/020463 A1 | 2/2006 |
| WO | 2007/022790 A1 | 3/2007 |
| WO | 2007/115295 A2 | 10/2007 |
| WO | 2008/011410 A2 | 1/2008 |
| WO | 2008/089537 A1 | 7/2008 |
| WO | 2009-011774 A2 | 1/2009 |
| WO | 2009-029074 A1 | 3/2009 |
| WO | 2009/108318 A2 | 9/2009 |
| WO | 2010/045749 A1 | 4/2010 |
| WO | 2010/065015 A1 | 6/2010 |
| WO | 2011/056690 A2 | 5/2011 |
| WO | 2011/066053 A2 | 6/2011 |
| WO | 2011-091349 A2 | 7/2011 |
| WO | 2012/015976 A1 | 2/2012 |
| WO | 2013/020123 A2 | 2/2013 |

* cited by examiner

SPINAL STABILIZATION SYSTEM

CROSS-REFERENCE TO RELATED APPLICATIONS

This application claims priority to U.S. Provisional Application No. 61/794,543, filed Mar. 15, 2013. The entire disclosure of U.S. Provisional Patent Application No. 61/794,543 is incorporated herein by reference.

FIELD OF THE INVENTION

The present invention relates generally to the field of medical apparatus and methods for using the same. More specifically, the present invention relates to systems and methods for treating spinal conditions, and specifically for systems for stabilizing vertebrae in the spinal column. More specifically, the present invention relates to interlaminar vertebral stabilization devices for placement between adjacent vertebra and including supporting devices for stabilization of the vertebral segments above and below the vertebra being treated.

BACKGROUND OF THE INVENTION

Injury to and/or diseases of the spine frequently result in damage to or abnormalities in the vertebrae, the intervertebral discs, the facet joints and to the connective tissue and ligaments around the spine. Such damage or abnormalities may result in spinal instability causing misalignment of the vertebral column and wear of the intervertebral discs and vertebral bony surfaces, a chronic and progressive deterioration which typically results in severe pain, loss or restriction of motion, and eventually, loss of mobility of the individual suffering from the condition.

One treatment option for addressing spinal disorders is via surgical intervention and the placement of fusion, stabilization and/or repair devices on or adjacent to the spine or between adjacent vertebrae. Certain surgical procedures are irreversible, for example, fusion techniques using bone grafts or synthetic implants to fuse vertebra, and may also significantly alter vertebral range of motion. Other procedures, for example procedures for installing spinal implants or pedicle screw systems for fixating two or more vertebrae, are intricate, time consuming and highly invasive. Alternative solutions include the insertion of interspinous or intralaminar spacers in the space between adjacent vertebrae to control relative motion between and to stabilize the two vertebrae. However, the stabilization does not extend above or below the insertion point, leaving the remaining portions of the spinal column subject to unstable motion and the potential damage resulting therefrom.

Various prior art systems have attempted to address the problems described above. U.S. Pat. No. 5,645,599 issued to Samani on Jul. 8, 1977 (the '599 patent), discloses an interspinal implant device having a generally u-shaped, spring-like configuration for insertion between the spinal processes of adjacent vertebrae. Samani's device includes opposing pairs of upwardly and downwardly extending brackets adapted to be secured to the spinal process, thereby providing for flexible positioning of the adjacent vertebrae. However, the apparatus of the '599 patent does not attribute to the overall stability of the spinal column; its effect being limited to the two specific vertebrae to which it is attached. It is also difficult to attach multiple devices configured in accordance with Samani's disclosure at adjacent segments due to interference of the bracket portions.

Hochschuler et al disclose various intra-laminar stabilization systems in U. S. Patent Application Publication No. US 2009/0202150 published on August 13, 2009 (the '150 publication), and in U. S. Patent Application Publication No. US 2011/0106163 published on May 5, 2011 (the '163 publication). The '150 publication discloses a pair of oppositely disposed hook members that are translationally positioned on a rod and adapted to engage the laminar regions of adjacent vertebra and maintain a preselected spacing there between. However, the apparatus of the '150 publication does not stabilize other vertebrae in the spinal column, its effect being limited to the two adjacent vertebrae which it engages.

The Hochschuler et al. '163 publication discloses an interlaminar stabilizing system which includes a structure adapted to be disposed between two adjacent vertebrae as described above with respect to the apparatus of the '150 publication. The '163 structure further includes a support structure which is secured to the second vertebra to further restrict the interval spacing between the adjacent vertebrae. However, the system of the '163 disclosure also does not stabilize the vertebrae in the remaining portions of the spinal column for the reasons set forth above.

Moreover, none of the known prior art systems address the problem of "transition syndrome" or "adjacent segment disease" associated with fusion of adjacent vertebrae. In fusion, if a motion segment is eliminated via fusion, the unfused adjacent segments above and below the fused vertebrae take up and bear the additional forces induced by bending and rotational movement of the spine, which may result in so-called "transition syndrome" over the long term. In addition, none of the prior art systems provide for augmenting previously installed spinal hardware to enhance stability, adjust intervertebral distraction, and so forth.

Accordingly, a need exists for an improved spinal stabilization system which provides both flexibility and stability to the spinal column and which addresses the combination of problems not solved by the prior art.

SUMMARY OF THE INVENTION

It is therefore an object of the present invention to provide an improved spinal stabilization system for maintaining preselected spacing and movement between adjacent vertebrae and also for providing overall stability to the spinal column.

In one embodiment, a spinal stabilization system is provided which includes at least one interlaminar member adapted to be inserted between two adjacent vertebrae and a stabilizing structure for stabilizing the vertebrae at least one layer above and below the two adjacent vertebrae.

In another embodiment, a spinal stabilization system is provided which includes a blocking member to limit movement of adjacent vertebrae to prevent narrowing of the spinal canal and nerve compression.

In yet another embodiment, a spinal stabilization system is provided which includes at least one adjustable cross-linking member to enhance stability of the spine.

These and other objects and features of the present invention will be apparent from the accompanying description of the invention, diagrams and supplemental supporting materials provided herein.

DESCRIPTION OF THE INVENTION

It should be noted that the present description is by way of illustration only, and that the concepts and examples presented herein are not limited to use or application with any single system or methodology. Hence, while the details of the system and methods described herein are for the convenience of illustration and explanation with respect to the exemplary embodiments, the principles disclosed may be applied to other types of spinal stabilization systems without departing from the scope of the present invention.

Figure 1:
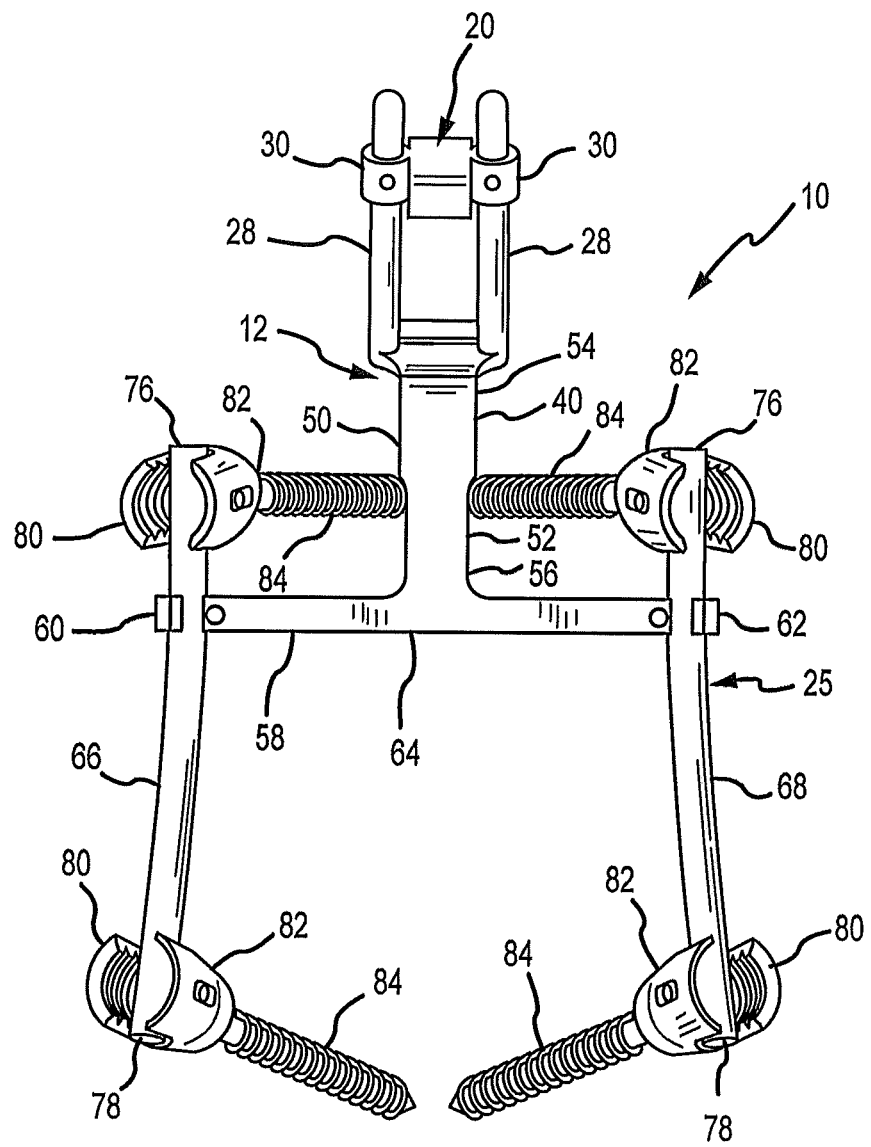
FIG. 1 is a front plan view of a spinal stabilization system of the present invention.
Figure 2:
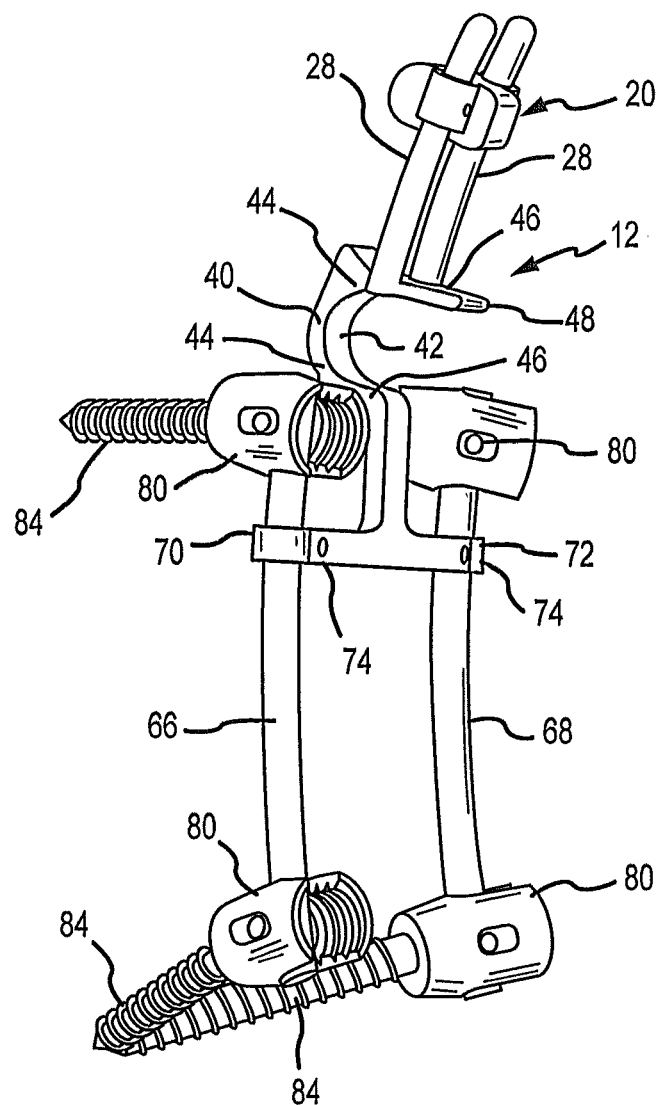
FIG. 2 is a side perspective view of a spinal stabilization system of the present invention.
Figure 3:
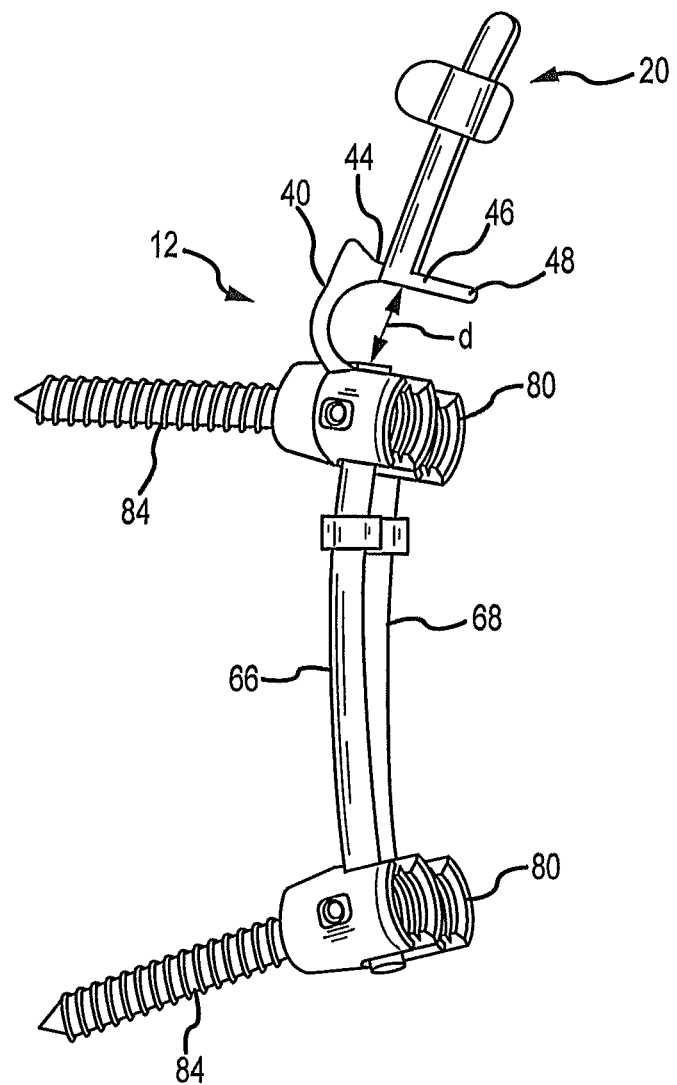
FIG. 3 is a side plan view of a spinal stabilization system of the present invention.
Figure 4:
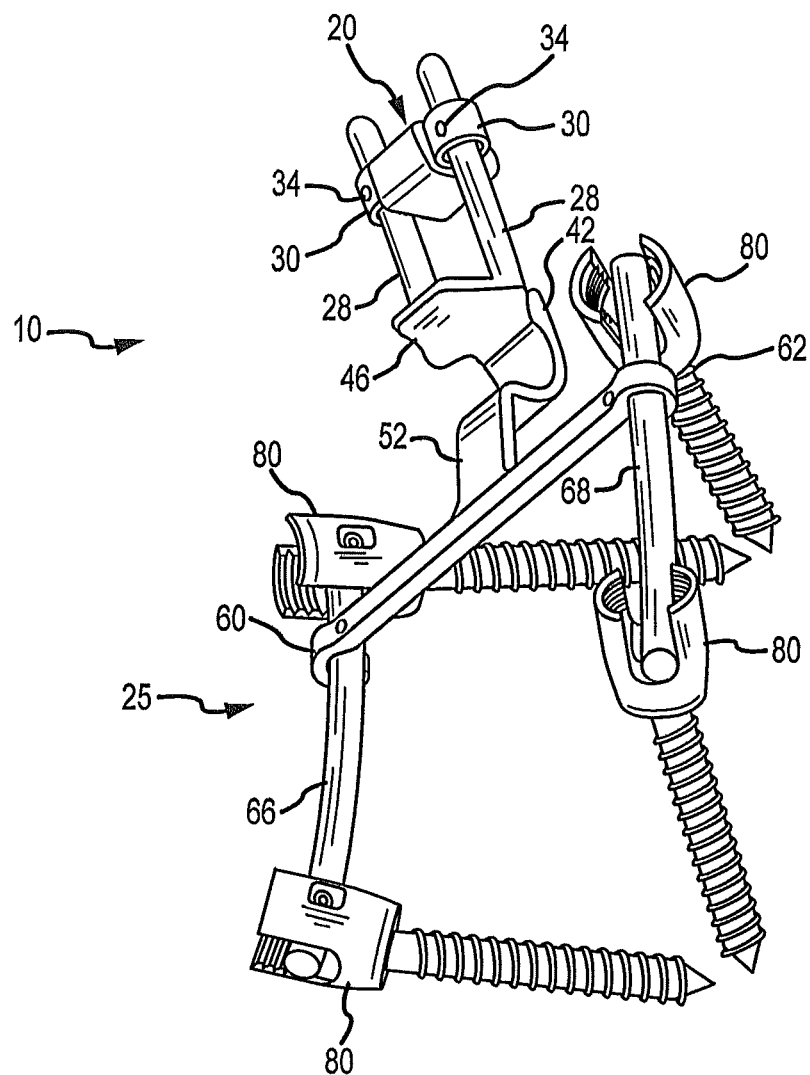
FIG. 4 is a bottom perspective view perspective view of a spinal stabilization system of the present invention.
Figure 5:
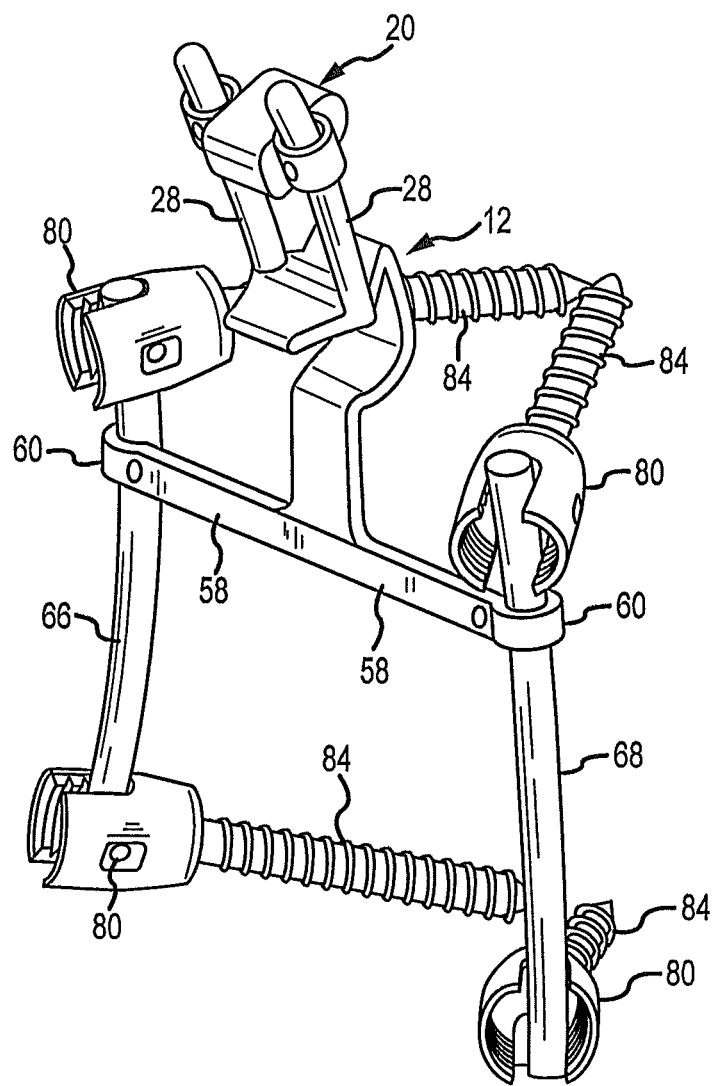
FIG. 5 is a top perspective view of a spinal stabilization system of the present invention.

Referring now to FIG. 1, a spinal stabilization system according to an embodiment of the present invention is shown generally at 10 (which for purposes of brevity will be referred to herein as "the system"). The system includes a first interlaminar member 12 adapted to be positioned between adjacent vertebra in a spinal column. As shown in greater detail in FIGS. 6 and 7, the interlaminar member 12 is shown positioned between a first vertebra 14 and a second adjacent vertebra 16 in a spinal column 18.

The system further includes a second interlaminar member 20 adapted to be positioned between the second vertebra 16 and a third vertebra 22 in the spinal column 18. Both the first and second interlaminar members are operatively connected to a support structure shown generally at numeral 25 in FIG. 1. By way of example, in the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

Figure 9:
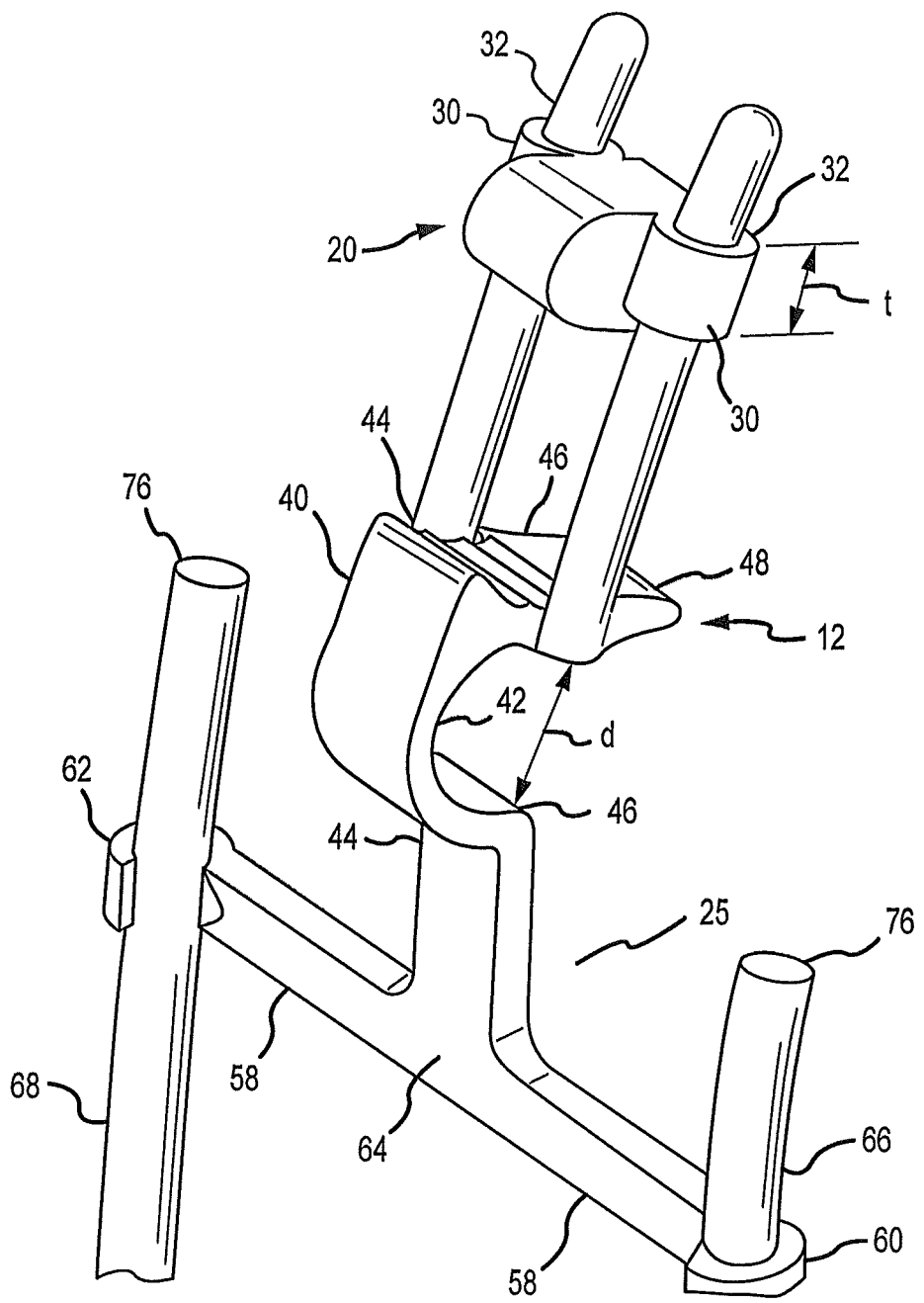
FIG. 9 is an exploded rear perspective view of a portion of the spinal stabilization system shown in FIGS. 6, 7 and 8.
Figure 10:
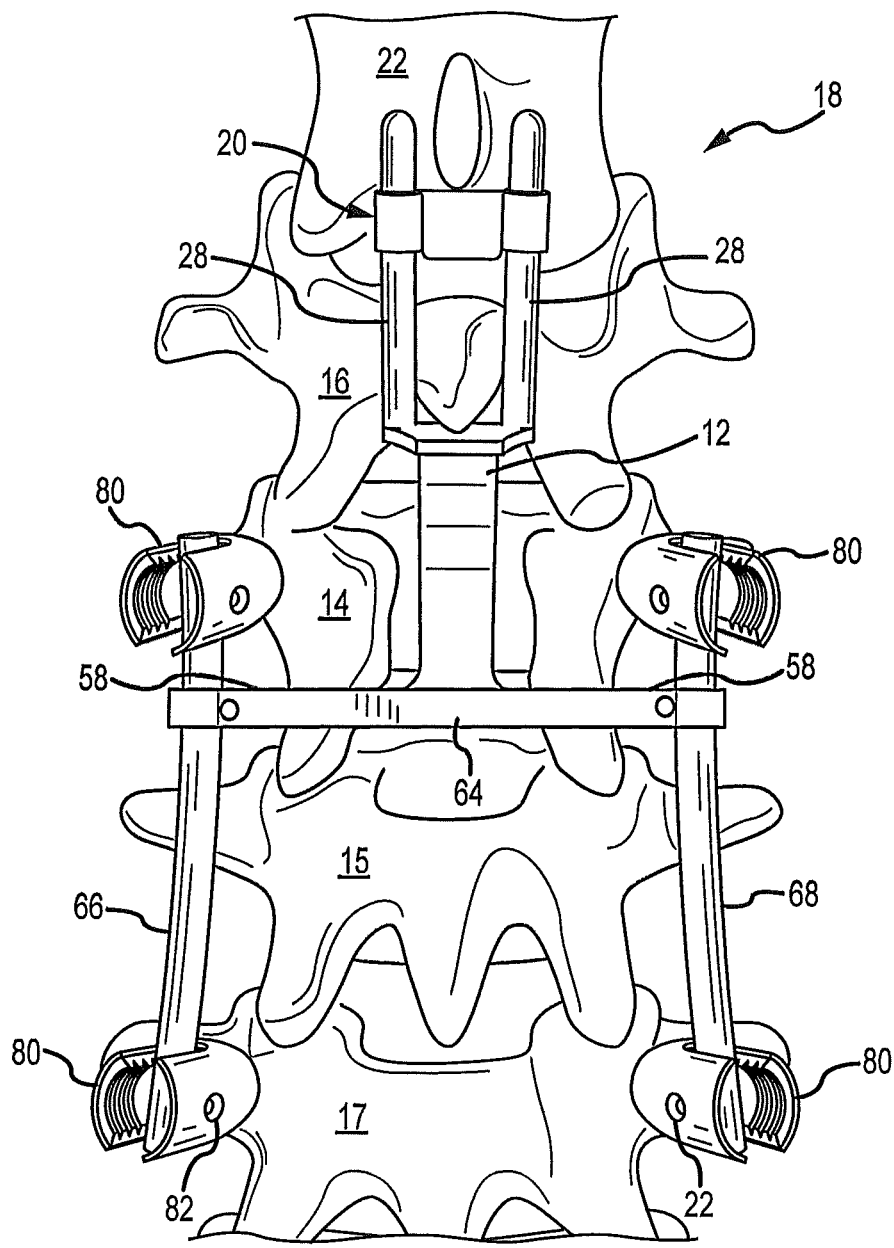
FIG. 10 is a front plan view of a spinal stabilization system of the present invention affixed to a spinal column.
Figure 11:
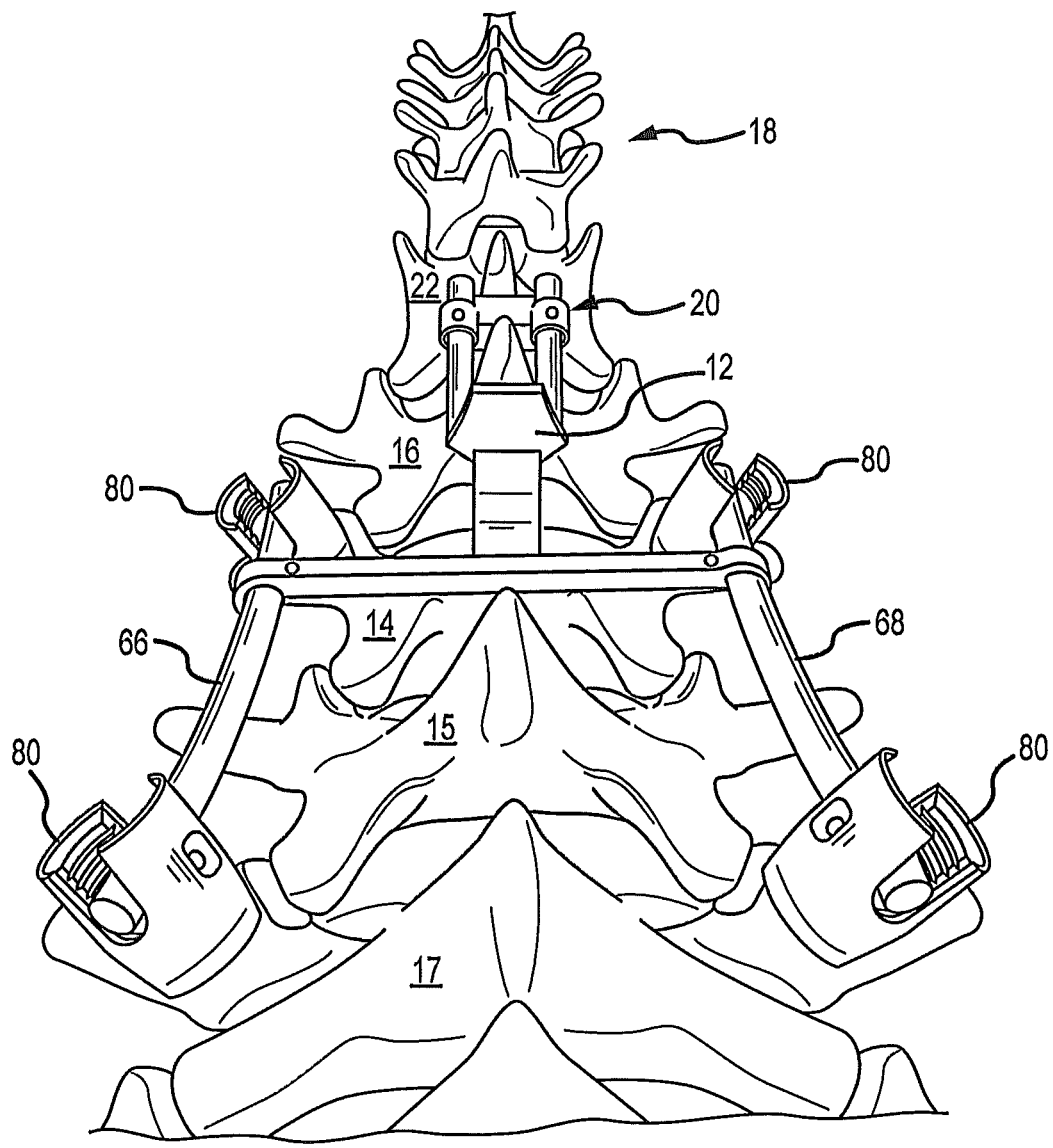
FIG. 11 is a bottom front perspective view of a spinal stabilization system of the present invention affixed to a spinal column.
Figure 12:
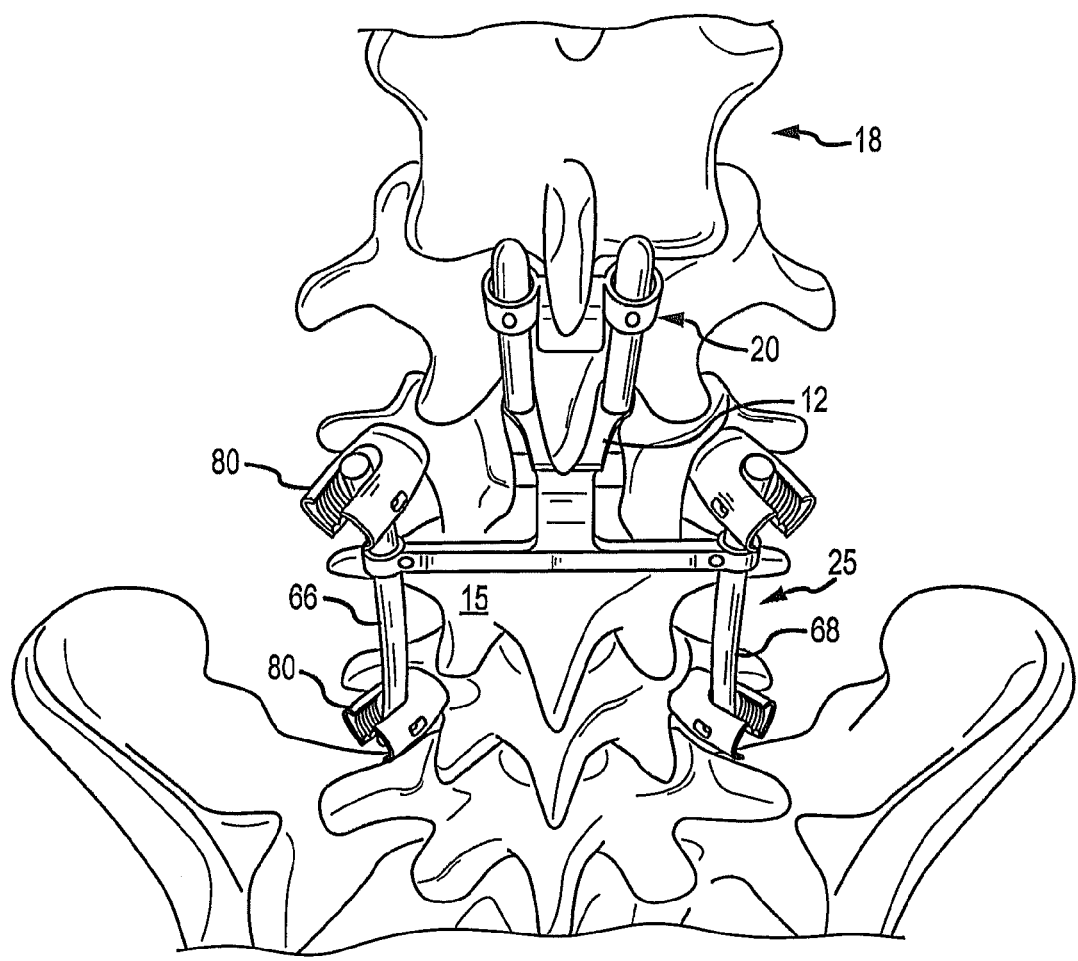
FIG. 12 is a top front perspective view of a spinal stabilization system of the present invention affixed to a spinal column.
Figure 13:
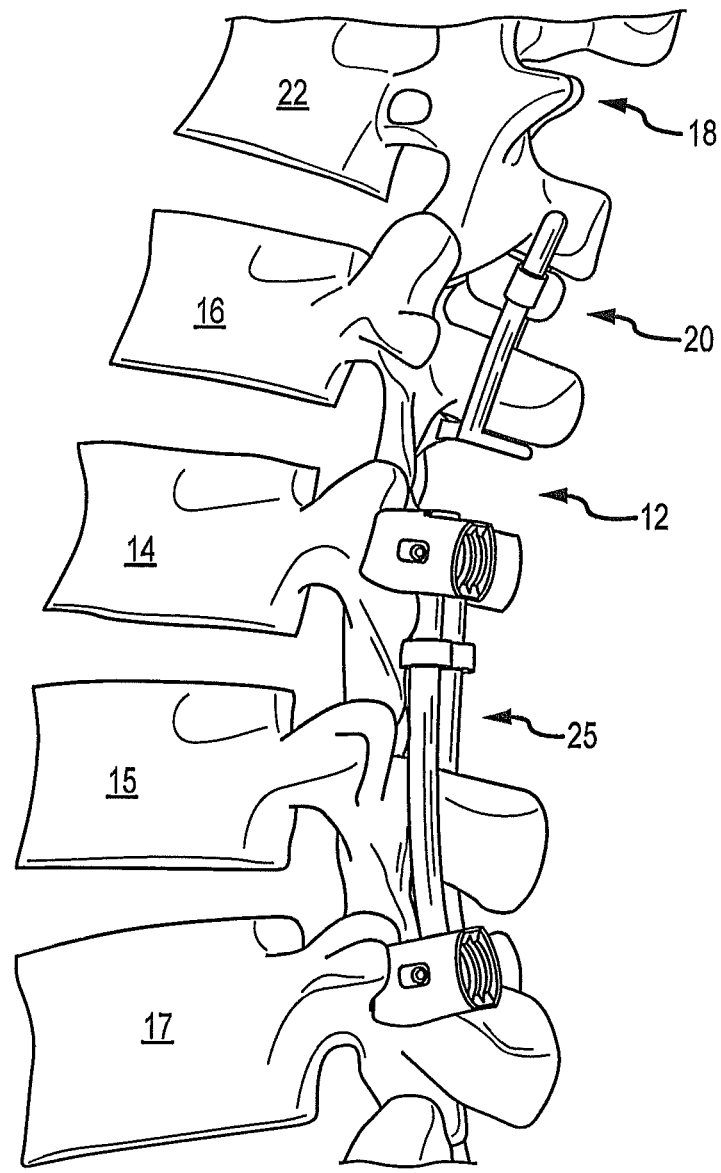
FIG. 13 is a side perspective view of a spinal stabilization system of the present invention affixed to a spinal column.

The support structure 25 comprises a pair of support members or guide rods 28 secured to the first interlaminar support member 12 and extending in a direction upwardly therefrom substantially parallel to one another. The second interlaminar member 20 includes a body portion 21 of a preselected thickness t, which is most clearly illustrated in FIG. 9. Thickness t is selected based upon the spacing between the second and third vertebrae and is intended to be smaller in size than the spacing to allow for flexion of the spinal column 18.

The body portion 21 further includes a pair of oppositely positioned ears 30 extending laterally outwardly from the body portion in opposing directions, each of the ears containing an aperture 32 structured and arranged to slideably receive one of the support members or guide rods 28. As will be discussed in greater detail below, the second interlaminar member is movably supported by upwardly extending support members or guide rods, and the position of the second interlaminar member 20 relative to the first interlaminar member 12 may be adjusted depending upon the dimensions of the specific spinal column on which the system is installed and the range of motion desired. Once the position of the second interlaminar member 20 has been selected, it is locked in place by a pair of set screws or other suitable fastening means 34 extending through each of the ears 30 and adapted to releaseably engage the respective guide rod extending therethrough.

Referring now to FIGS. 2, 3, 7 and 8, the first interlaminar member is 12 depicted in greater detail. The first interlaminar member comprises a U-shaped body 40 defined by an elastic midsection 42, two spaced apart end portions 44, and a pair of juxtaposed legs 46, each leg extending substantially parallel to one another from one of the respective ends in a direction generally outwardly away from the spinal column 18 (FIG. 7) and spaced apart a preselected distance d. Distance d is determined by the size of the first interlaminar member, which is, in turn, is selected based upon the spacing between the first and second vertebrae. The first interlaminar member is intended to fuse the first and second vertebrae. Accordingly, it is sized to be a tight fit, and the elastic properties of the U-shaped body 40 act as a spring or shock absorber in the interface between the two vertebrae. Further, the uppermost one of the legs 46 is longer that the lower one of the legs, thereby forming a handle 48 which may be used to insert and position the system during surgery.

Referring again to FIG. 1, the support structure 25 further includes a T-shaped frame member 50 operatively connected to the first and second interlaminar members 12 and 20 and extends generally downwardly therefrom in a direction substantially parallel to the spinal column 18. The T-shaped frame member has comprises an elongate body 52 having first and second end portions 54, 56, the first end portion being operatively connected to the first interlaminar member 12, and an elongate cross member 58. The cross member has first and second end portions 60, 62 and a midpoint 64 and is structured and arranged to be connected to the second end portion 56 of the body 52 at approximately the midpoint 64. Each of the ends 60, 62 of the cross member 58 are adapted to receive and adjustably secure first and second support members 66 and 68 respectively. In the embodiment shown, each of the end portions 60, 62 have an aperture 70, 72 formed therein respectively for receiving one of the support members 66, 68, each of which may be held in a preselected position by a set screw 74.

In the embodiment shown, by way of example only and not of limitation, the support members are in the form of guide rods 66, 68, each guide rod having an upper end 76 and a lower end 78. Each of the upper and lower ends of the support members 66, 68 has a securing device 80 slideably positioned thereon and adapted to be secured thereto by means of set screws 82. By way of example, each of the securing devices is shown in the form of a pedicle screw 84, each pedicle screw being structured and arranged to be secured to one of the vertebra of the spinal column 18.

Figure 6:
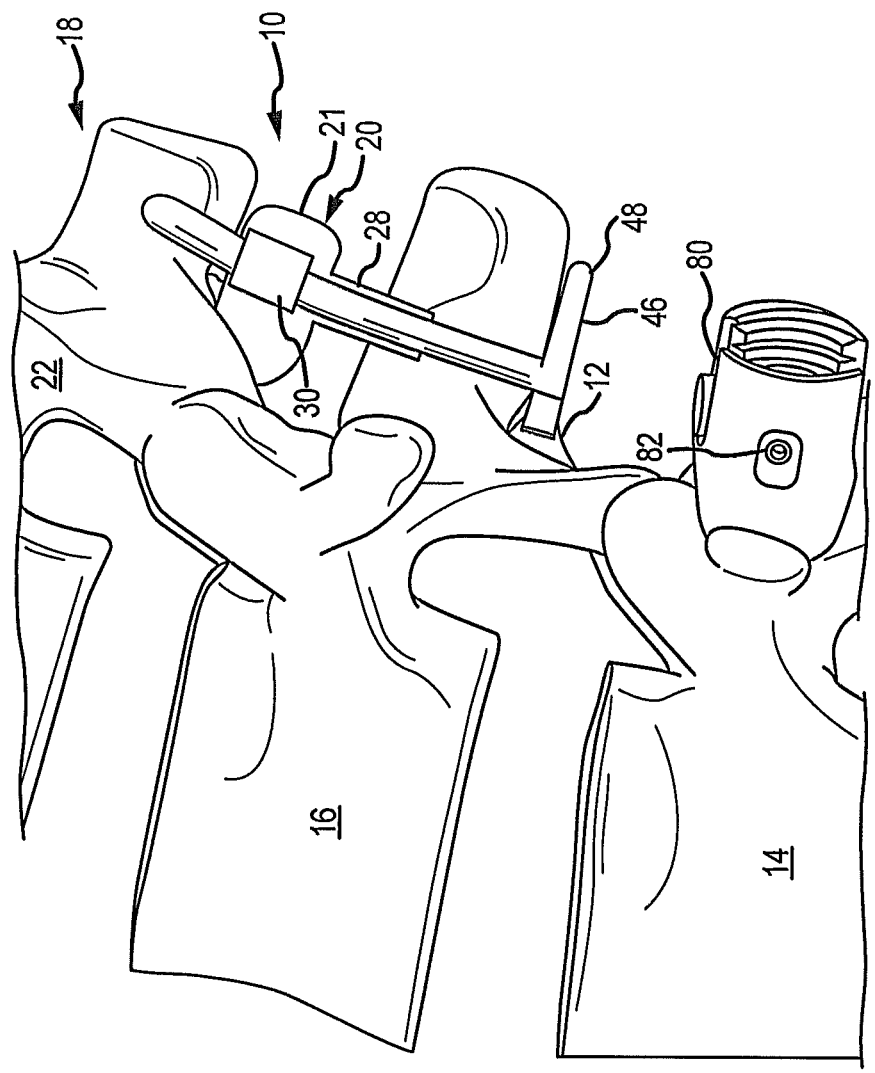
FIG. 6 is an enlarged side plan view of a portion of the spinal stabilization system of the present invention shown in FIG. 3 showing an upper portion of the stabilization system affixed to a spinal column.
Figure 7:
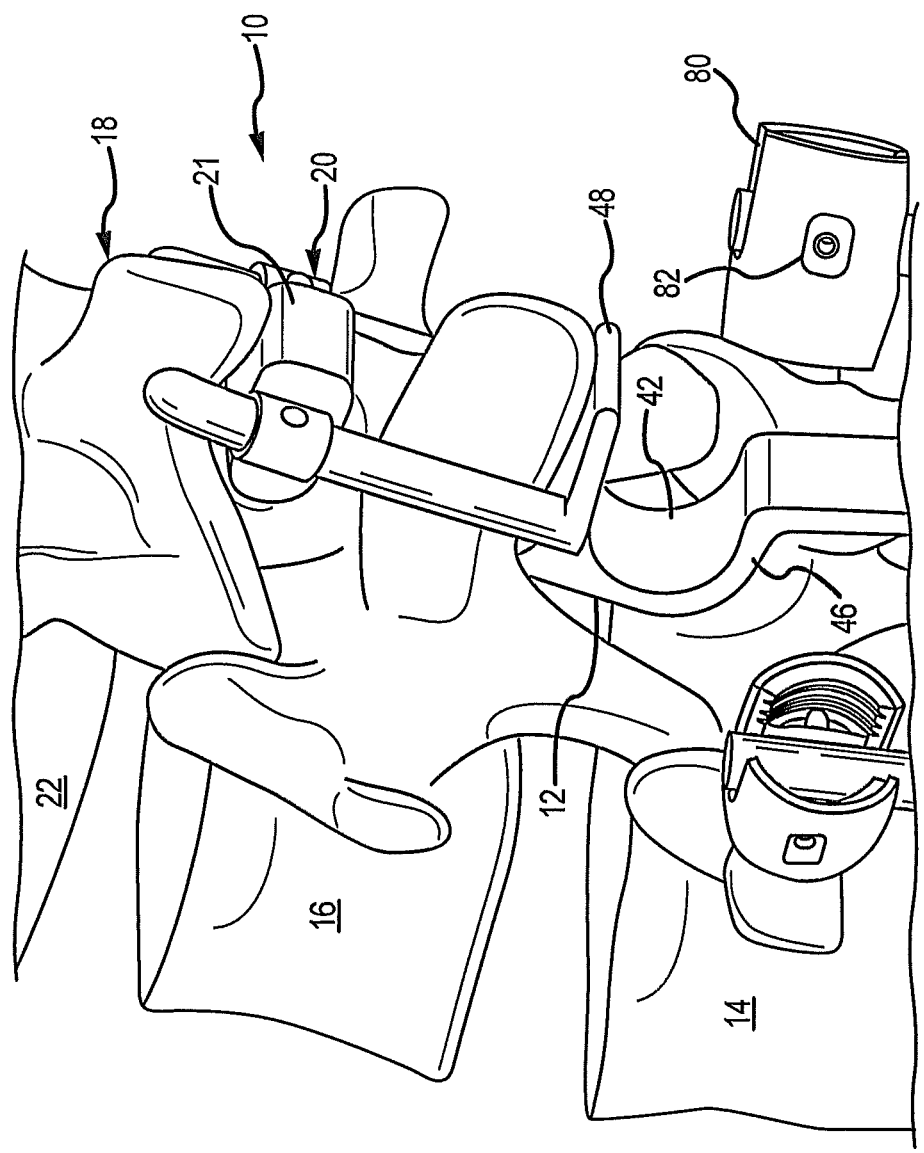
FIG. 7 is a side perspective view of a portion of the spinal stabilization system shown in FIG. 6.
Figure 8:
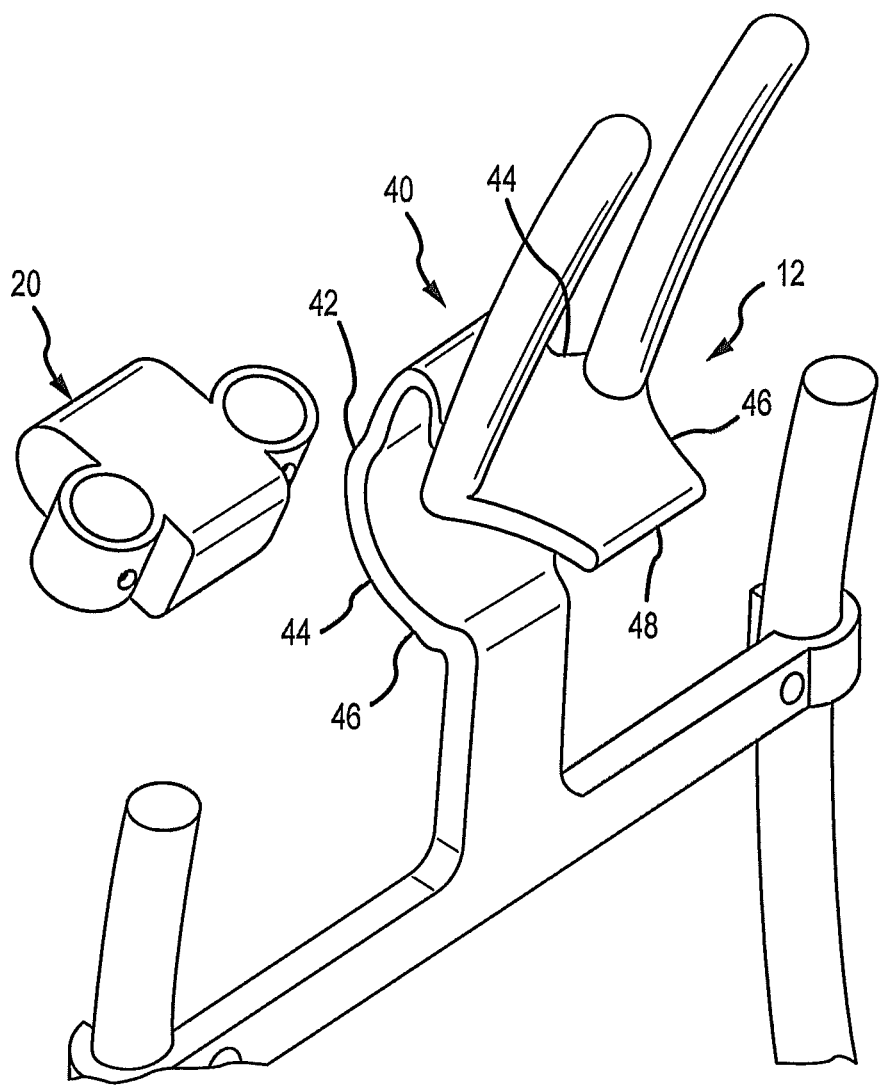
FIG. 8 is an exploded front perspective view of a portion of the spinal stabilization system shown in FIGS. 6 and 7.

The installation and operation of the spinal support system 10 of the present invention are illustrated in greater detail in FIGS. 6, 7, and 10-13. The system advantageously may be installed where other spinal fusion devices or similar medical apparatus are already in place to add stability to the spinal column above and below the installation point, to control flexion and/or rotational movement of the spine or selected vertebrae with respect to one another, and to prevent impingement of adjacent vertebrae, spinal processes, pedicle screws and medical hardware on one another. By way of example, as best shown in FIGS. 6 and 7, a surgeon may insert the system 25 into the space between adjacent vertebrae 14 and 16 by gripping handle 48 and making the insertion. The tight fitting U-shaped body 40 not only serves to control any motion between the adjacent vertebrae or even eliminate it entirely, thereby effectively fusing the vertebrae, but also serves as a dampening cushion or spring device by virtue of the spring-like elasticity of the body 40 translated to the vertebrae via legs 46. Thereafter, the second interlaminar member 20 may be selectively positioned intermediate vertebra 16 and vertebra 22 to permit flexion on a forward direction but to limit extension in the rearward direction and to limit compression of the spinal segment, thereby imparting enhanced stability to the spinal column above the fused vertebrae.

In a similar manner, support structure 25, via the T-shaped frame member 50 and support members or guide rods 66 and 68, provides support to the spinal processes located below the fused vertebrae 14 and 16. As shown in FIGS. 10-13, the pedicle screws 80 may be positioned in first vertebra 14 and in either vertebra 15 immediately adjacent to vertebra 14, or at a lower level as shown by vertebra 17, thus extending the stabilizing effect of the novel support system of the present invention to multiple levels in the spinal column 18. More than one level may be addressed simply by lengthening the rods 66 and 68 and slideably positioning multiple pedicle screws 80 thereon for selective positioning along the spinal column.

In one aspect, the cross member midpoint 64 may be configured, structured and arranged to be adjustably (e.g., pivotably or translatably) connected or secured to the second end portion 56 of the body 52 at approximately the midpoint 64 in order to allow a surgeon during the course of the surgical procedure to adjust and align components of the implant in relation to the patient's bony anatomy and in relation to support members 66 and 68.

In another aspect, elongate body 52 may be comprised of multiple pieces. For example, one or more linear racks may be configured in operable relation with gear mechanisms, thereby forming a ratchet device (not shown), in order to extend the distance between first and second end portions 54 and 56 thereby permitting a surgeon during the course of the surgical procedure to adjust and align components of the implant in relation to the patient's bony anatomy and subsequently securing them in place. For example, a ratchet mechanism configuration may permit the surgeon to progressively extend elements of the implant to better appose a lamina.

In yet another aspect, each of the ends 60, 62 of the cross member 58 may be configured to permit a degree of adjustability (e.g., pivotably or translatably) to receive and adjustably secure first and second support members 66 and 68 respectively. For example any cross-link variable adjustment mechanism or fastener known in the art may be employed to accomplish the desired fixation between the ends 60, 62 of the cross member 58 and first and second support members 66 and 68.

According to particular embodiments, interlaminar member 20 may be configured to permit connection to guide rods 28 via an approach that is substantially perpendicular to the longitudinal axis of guide rods 28. In other words, after the other components of the system have been implanted via a posterior approach to the posterior aspect of the spine the interlaminar member 20 may follow a generally similar approach trajectory and then secured to the guide rods 28 with, e.g., set screws in a similar manner to the engagement between the ends 60, 62 of the cross member 58 and first and second support members 66 and 68. Furthermore, in another aspect, an interlaminar member 20 may be used alone (and may alternatively be configured to be similar to the U-shaped body 40) and may be directly engaged with a first and second support members 66 and 68 and positioned between the lamina and spinous processes of the spine.

In particular aspects, the different elements of the system may be configured with tool engagement features in order to permit a surgeon to grasp the implant with a tool assembly or insertion tool to ease implantation of the various components. For example, the insertion tool may be configured as a pair of pliers or hemostats. As another example, a threaded portion of a tool assembly may reversibly secure to a complementary threaded portion of the implant in order to ease implantation. E.g., a tool assembly may be comprised of a cannulated shaft with a retainer shaft housed substantially within, the retainer shaft further configured with a threaded portion at its distal end which may extend out of a distal end of the retainer shaft and a handle located and attached to a proximal end of the retainer shaft; the distal end of the retainer shaft may have a feature that permits rotation of the retainer shaft via another tool, such as the mechanical arrangement that exists between a wrench and nut, in order to secure the tool assembly to the implant. After implantation of the implant the tool assembly may be decoupled and removed.

Changes may be made in the above methods and systems without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. A spinal stabilization system comprising:
   a first interlaminar member adapted to be positioned between a first vertebra and a second vertebra in a spinal column; the first interlaminar member including a U-shaped body having a midsection, and two spaced apart end portions, and a pair of juxtaposed legs extending substantially parallel to one another from one of the respective ends in a direction generally outwardly away from the spinal column;
   a second interlaminar member adapted to be positioned between the second vertebra and a third vertebra positioned adjacent to and above the first vertebra in the spinal column; and
   a support structure operatively connected to the first and second interlaminar members, the first vertebra and at least one vertebra positioned below the first vertebra in the spinal column, the support structure including a T-shaped frame member operatively connected to the first and second interlaminar members and extending generally downwardly therefrom in a direction substantially parallel to the direction of the spinal column, the T-shaped frame member including an elongate body having first and second end portions, the first end portion being operatively connected to the first interlaminar member, and an elongate cross member having first and second end portions and a midpoint, the elongate cross member being operatively connected approximately at the midpoint to the second end portion of the body.

2. The system of claim 1 wherein the support structure includes a pair of support members secured to the first interlaminar member extending upwardly therefrom in a direction substantially parallel to one another.

3. The system of claim 2 wherein the second interlaminar member is moveably supported by the upwardly extending support members.

4. The system of claim 3, wherein the second interlaminar member is adjustably movable to a preselected position on the upwardly extending support members relative to the first interlaminar member in response to a dimension of the spinal column and a range of motion desired, and wherein the system further includes a fastener adapted to secure the position of the second member relative to the support member such that once the position of the second interlaminar member has been selected, the second interlaminar member is locked in place relative to the support members by the fastener.

5. The system of claim 4, wherein the second interlaminar member includes a body portion configured to support the fastener whereby the fastener extends through the body portion and is adapted to releaseably engage a support member of the pair of support members when extending therethrough.

6. The system of claim 2, wherein the second interlaminar member includes a body portion comprising a pair of oppositely positioned ears extending laterally outwardly from the body portion in opposing directions, each of the ears including an aperture formed therein, each aperture being structured and arranged to slideably receive one of the support members.

7. The system of claim 1, wherein the elongate cross member is adjustably connected to the second end position of the body, whereby the elongate cross member is pivotally or translatably movable with respect thereto.

8. The system of claim 7, wherein the elongate body includes at least one linear rack, the rack being structured and arranged to progressively extend the distance between the first and second end portions of the elongate body of the T-shaped frame member.

9. The system of claim 8, further including a gear mechanism operatively connected to the at least one linear rack, the gear mechanism and the at least one linear rack forming a ratchet device configured to permit the progressive extension.

10. The system of claim 1 wherein the second interlaminar member is structured and arranged to fit loosely between the second vertebra and the third vertebra.

11. The system of claim 10, wherein the second interlaminar member includes a body portion of a preselected thickness, the preselected thickness being based upon spacing between the second and third vertebrae whereby the preselected thickness of the body portion is smaller in size than the spacing to allow for a flexion of a portion of the spinal column.

12. The system of claim 1 further including first and second support members adjustably secured to the first and second ends of the elongate cross member respectively.

13. The system of claim 12 where each of the first and second support members includes an upper and a lower end, each of the upper and lower ends having a securing device slideably positioned thereon, each securing device being structured and arranged to be secured to a vertebra in the spinal column.

14. The system of claim 1, wherein the pair of juxtaposed legs comprises an uppermost leg and a lowermost leg, the first end portion of the elongate body being operatively connected to the first interlaminar member at the lowermost leg and wherein the uppermost leg is longer that the lowermost leg.

15. The system of claim 14, wherein the uppermost leg forms a handle adapted to facilitate insertion and positioning of the system during surgery.

16. The system of claim 1 wherein the first interlaminar member is structured and arranged to fit tightly between the first vertebra and the second vertebra.

17. The system of claim 1, wherein the midsection is elastic.

18. The system of claim 1, wherein the support structure and the first interlaminar member are integrally formed from a single piece of material.

19. The system of claim 1, further including means for connecting the first interlaminar member to the support structure, the connecting means comprising at least one of: a) a hinge; b) a pin; or c) a threaded fastener.

20. The system of claim 1, wherein each of the first and second end portions of the elongate cross member comprises a variable adjustment mechanism configured to pivotably or translatably receive and adjustably secure to the first and second support members.

21. A system for treating a patient's spinal column, the system comprising:
a spinal stabilization system including a first interlaminar member adapted to be positioned between a first vertebra and a second vertebra in a spinal column; the first interlaminar member including a U-shaped body having a midsection, and two spaced apart end portions, and a pair of juxtaposed legs extending substantially parallel to one another from one of the respective ends in a direction generally outwardly away from the spinal column;
a second interlaminar member adapted to be positioned between the second vertebra and a third vertebra positioned adjacent to and above the first vertebra in the spinal column; and
a support structure operatively connected to the first and second interlaminar members, the first vertebra and at least one vertebra positioned below the first vertebra in the spinal column, the support structure including a T-shaped frame member operatively connected to the first and second interlaminar members and extending generally downwardly therefrom in a direction substantially parallel to the direction of the spinal column, the T-shaped frame member including an elongate body having first and second end portions, the first end portion being operatively connected to the first interlaminar member, and an elongate cross member having first and second end portions and a midpoint, the elongate cross member being operatively connected approximately at the midpoint to the second end portion of the body and an insertion tool configured to reversibly secure to a tool engagement portion of the spinal stabilization system, the insertion tool being adapted to permit a surgeon to grasp the system with the insertion tool whereby implantation of the system in the patient's spinal column is facilitated.

22. The system of claim 21, wherein the insertion tool comprises a pair of pliers or hemostats.

23. The system of claim 22, wherein the tool engagement portion includes a threaded portion and wherein the insertion tool includes a threaded portion configured to reversibly secure to the threaded portion of the tool engagement portion of the spinal stabilization system.

24. The system of claim 23, wherein the insertion tool includes a cannulated shaft and a retainer shaft housed substantially within the cannulated shaft, the retainer shaft including a distal end and a proximal end opposite the distal end, the distal end of the retainer shaft comprising the threaded portion thereof and the proximal end of the retainer shaft comprising a handle.

* * * * *

UNITED STATES PATENT AND TRADEMARK OFFICE
CERTIFICATE OF CORRECTION

PATENT NO. : 9,510,872 B2
APPLICATION NO. : 14/209138
DATED : December 6, 2016
INVENTOR(S) : Donner et al.

Page 1 of 1

It is certified that error appears in the above-identified patent and that said Letters Patent is hereby corrected as shown below:

Column 7, Line 45 should read:
member is adjustably connected to the second end portion Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*